(12) United States Patent
Cavanagh et al.

(10) Patent No.: US 6,610,897 B2
(45) Date of Patent: Aug. 26, 2003

(54) WOUND HEALING SYSTEM AND METHOD OF USE

(76) Inventors: Peter R. Cavanagh, 1352 Deerfield Dr., State College, PA (US) 16803; Jan S. Ulbrecht, 1120 Oak Tree La., Boalsburg, PA (US) 16827

( * ) Notice: Subject to any disclaimer, the term of this patent is extended or adjusted under 35 U.S.C. 154(b) by 0 days.

(21) Appl. No.: 09/817,412

(22) Filed: Mar. 26, 2001

(65) Prior Publication Data

US 2002/0138030 A1 Sep. 26, 2002

(51) Int. Cl.[7] .......... A61F 13/00; A61F 5/14; A61F 5/37; A61F 13/06
(52) U.S. Cl. .......... 602/54; 602/60; 602/61; 36/140; 128/882; 128/893
(58) Field of Search .......... 602/5, 10, 23, 602/27, 28, 29, 60–62, 66; 128/882, 888–890, 892–894; 36/43, 44, 71, 88, 93, 95, 110, 140, 145

(56) References Cited

U.S. PATENT DOCUMENTS

| 4,235,027 A | * | 11/1980 | Singh .......... 36/43 |
| 5,197,942 A | | 3/1993 | Brady |
| 5,329,705 A | | 7/1994 | Grim et al. |
| 5,483,757 A | | 1/1996 | Frykberg |
| 5,768,803 A | * | 6/1998 | Levy .......... 36/43 |
| 5,797,862 A | | 8/1998 | Larmont |
| 6,083,185 A | | 7/2000 | Larmont |

\* cited by examiner

Primary Examiner—Kim M. Lewis
(74) Attorney, Agent, or Firm—John J. Elnitski, Jr.

(57) ABSTRACT

The present invention is a wound healing system and method of use to address the healing of wounds found on a foot of a patient. The wound healing system provides an apparatus and method of protecting and healing foot wounds, especially foot ulcers of diabetic patients. The wound healing system can be used on a wound found on almost any area of the bottom of a foot. The wound healing system includes a method of reducing the mechanical load on a wound, allowing the patient to walk while the system is in use, allowing the patient to access and attend to the foot, allowing different methods of treating a foot wound, and providing a kit with which medical personnel can easily fit the patient with the apparatus.

19 Claims, 23 Drawing Sheets

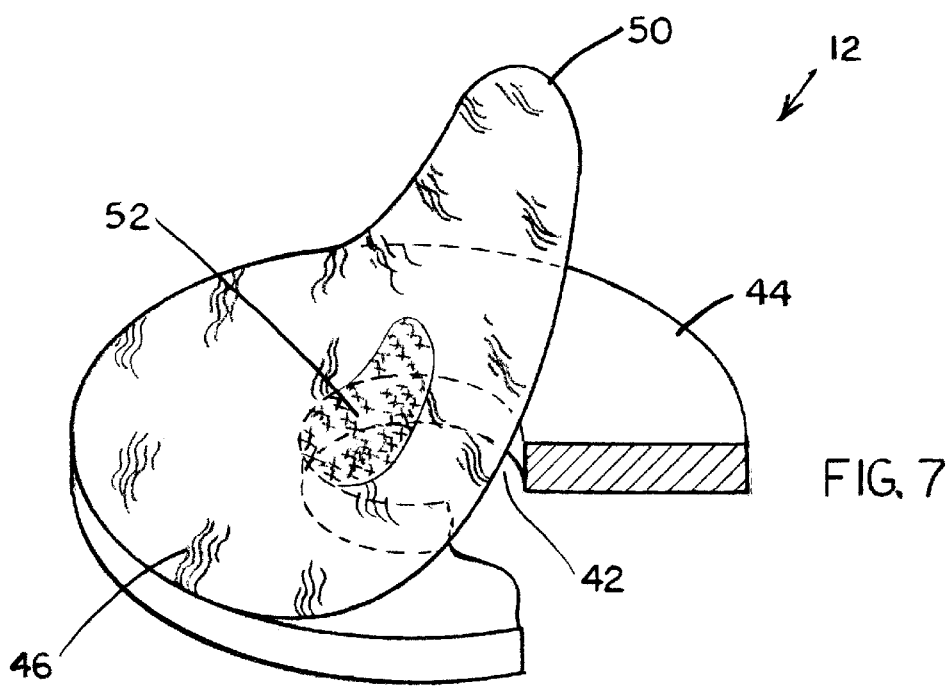
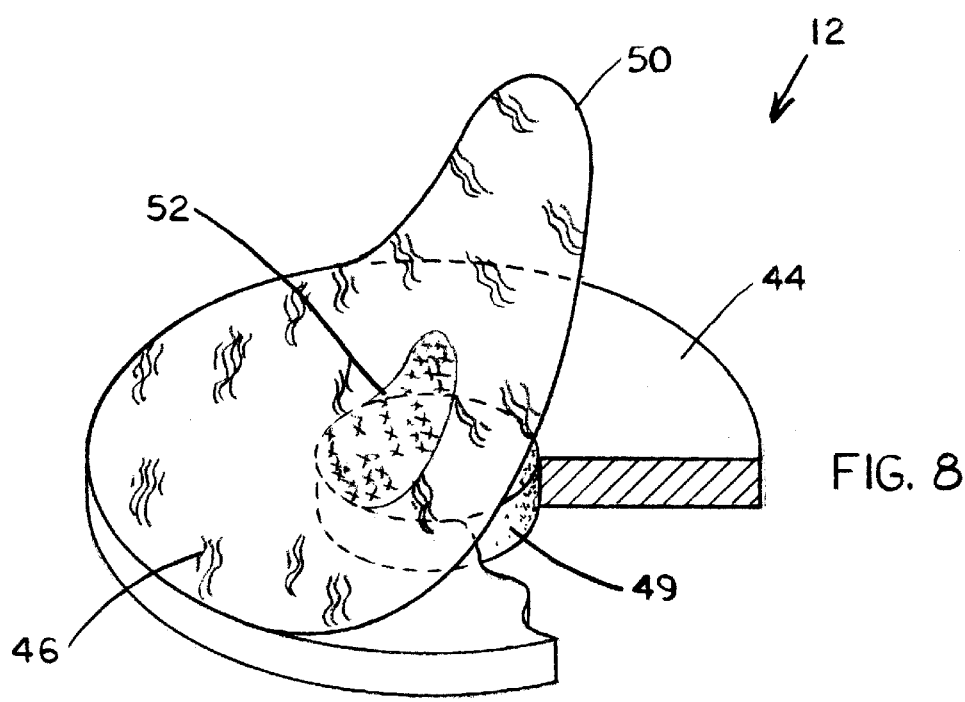

WOUND HEALING SYSTEM AND METHOD OF USE

BACKGROUND

It is known that foot wounds in diabetic patients represent a significant public health problem throughout the world. Treatment of such wounds has been focused on amputation and not on limb salvage, as many of the wounds have not been properly treated. Improper treatment can be attributed to lack of an easy treatment method and inconvenience to the patient in using current methods. There is a need to prevent amputation by healing such wounds at an early stage.

Foot wounds in patients with diabetes develop because of a process called neuropathy. Diabetes causes loss of sensation such that skin injury and complete breakdown (ulcer) can develop with no or minimal pain. These wounds tend not to heal because of ongoing mechanical trauma not felt at all by the patient as painful. Such wounds can only be healed by protecting them from mechanical trauma. Small plantar ulcers in diabetic patients are usually seen by primary care practitioners and endocrinologists. The present method for healing plantar ulcers is a total contact cast for the foot, which provides complete mechanical protection. This method is not ideally suited for either of these practice settings, because it requires skilled and specialized care in application, along with frequent follow up. Most patients perceive the cast to be an inconvenience at the early stages of such a wound, while perceiving that such a wound is not serious matter. The alternative to the cast is to ask the patient to be non-weight bearing through the use of a wheelchair, crutches, or a walker, which provide complete mechanical protection only with complete patient compliance. This alternative rarely proves to be effective in healing wounds within a reasonable time period, due to human nature.

What is needed is a treatment that primary care physicians or their staff can employ to treat ulcers and other wounds on the feet. Also, what is needed is a treatment that allows patients to be able to continue their active lives when they have a foot wound, yet promotes healing of the wound. Unfortunately, due to human nature, the perceived insult and inconvenience of using healing methods that are currently available is sufficient to discourage their use by the patient.

It is an object of the present invention to provide a wound healing system which reduces mechanical load on a wound.

It is another object of the present invention to provide a wound healing system which is easy to employ by medical personnel.

It is another object of the present invention to provide a wound healing system in which will not be rejected by the patient.

SUMMARY OF THE INVENTION

The present invention is a wound healing system and method of use to address the healing of wounds found on a foot of a patient. The wound healing system provides an apparatus and method of protecting and healing foot wounds, especially foot ulcers of diabetic patients. The wound healing system includes a load relieving dressing, foot pad and a dressing opening. The load relieving dressing is attached to an area about the wound of the foot, whereby the load relieving dressing provides support to the foot in the area and relieves load on the wound. The foot pad fits into footwear. The dressing opening is in the foot pad and is sized to securely receive the load relieving dressing.

BRIEF DESCRIPTION OF THE DRAWINGS

FIG. 7 is a perspective view of another example of the load relieving dressing according to the present invention;

FIG. 8 is a perspective view of another example of the load relieving dressing according to the present invention;

DETAILED DESCRIPTION OF THE INVENTION

The present invention is a wound healing system and method of use to address the healing of wounds found on a foot of a patient. The wound healing system provides an apparatus and method of protecting and healing foot wounds, especially foot ulcers of diabetic patients. The wound healing system can be used on a wound found on almost any area of the bottom of a foot. The wound healing system includes a method of reducing the mechanical load on a wound, allowing the patient to walk while the system is in use, allowing the patient to access and attend to the foot, allowing different methods of treating a foot wound, and providing a kit with which medical personnel can easily fit the patient with the apparatus.

Figure 1:
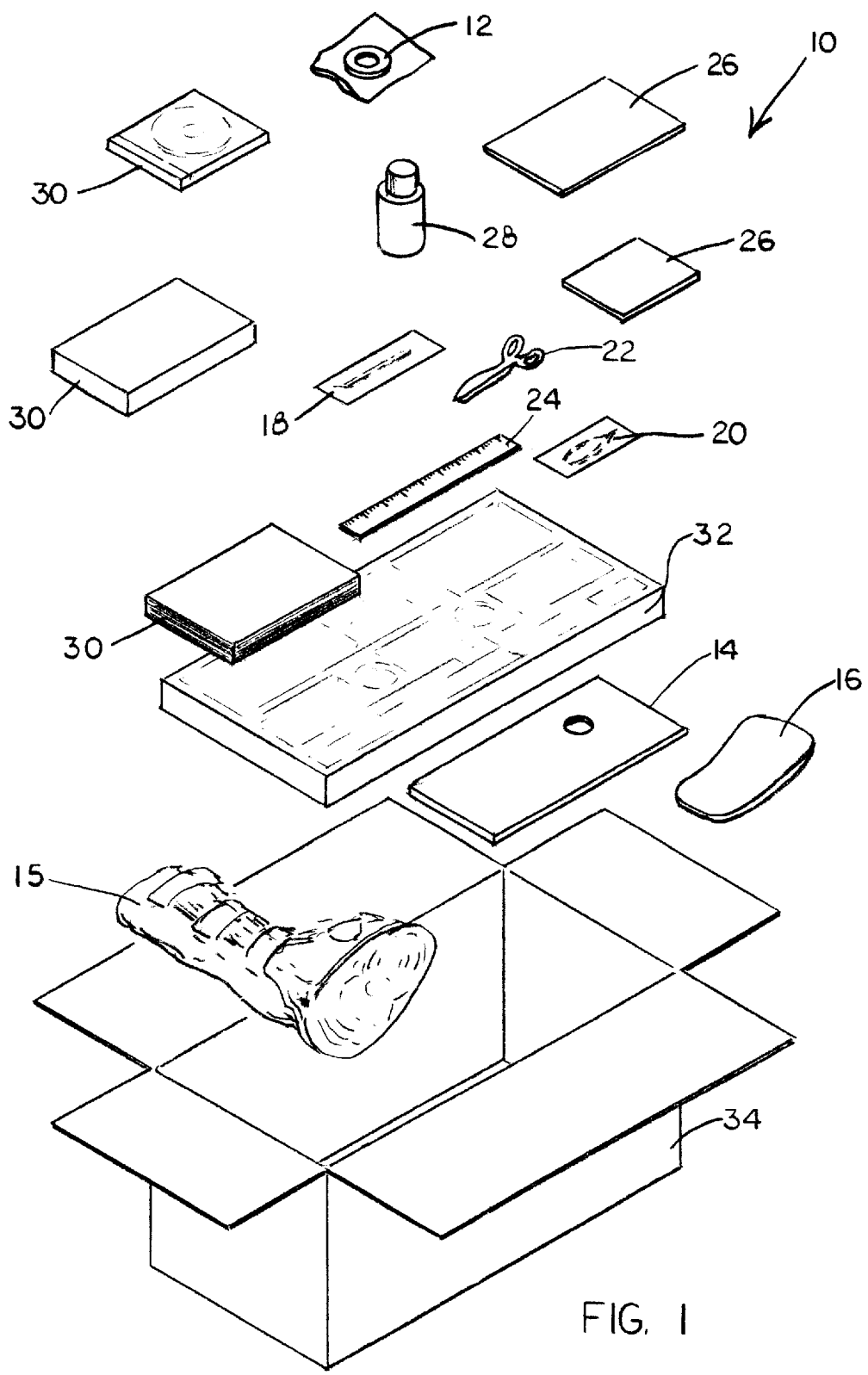
FIG. 1 is an exploded view of a kit containing a wound healing system according to the present invention.

FIG. 1 shows the wound healing system 10 in a kit form which can be utilized by medical personnel. The main components of the wound healing system 10 are a load relieving dressing 12 and a foot pad 14 which receives the load relieving dressing 12. Other components which can be included as part of the kit are a boot 15, cushion pad 16, surgical blade 18, tweezers 20, scissors 22, ruler 24, wound treatment pads 26, wound cleanser 28 and educational materials 30. The boot 15 is used to allow the patient to be mobile, without being restricted to a non-weight bearing device, such as a wheelchair or crutches. Other types of footwear can be substituted for the known medical boot 15 that is shown. The cushion pad 16 provides additional cushioning in the boot 15. The surgical blade 18, tweezers 20, wound treatment pads 26 and wound cleanser 28 are attending materials instruments for treating a wound on a foot. The ruler 24 or other type of measuring instrument is for assessing the size of the wound, as well as sizing the foot and foot pad 14. The scissors 22 is a cutting instrument for cutting the foot pad 14 according to the size of the foot and the boot 15. The educational materials 30 are for educating the user of the kit and the patient with the foot wound as to the proper use of the wound healing system 10. The education materials 30 can include a CD for use on a computer, video tape and booklets. Foam board 32 is also show as part of the kit and is simply used to separate materials in a box 34 containing the kit.

Figure 2:
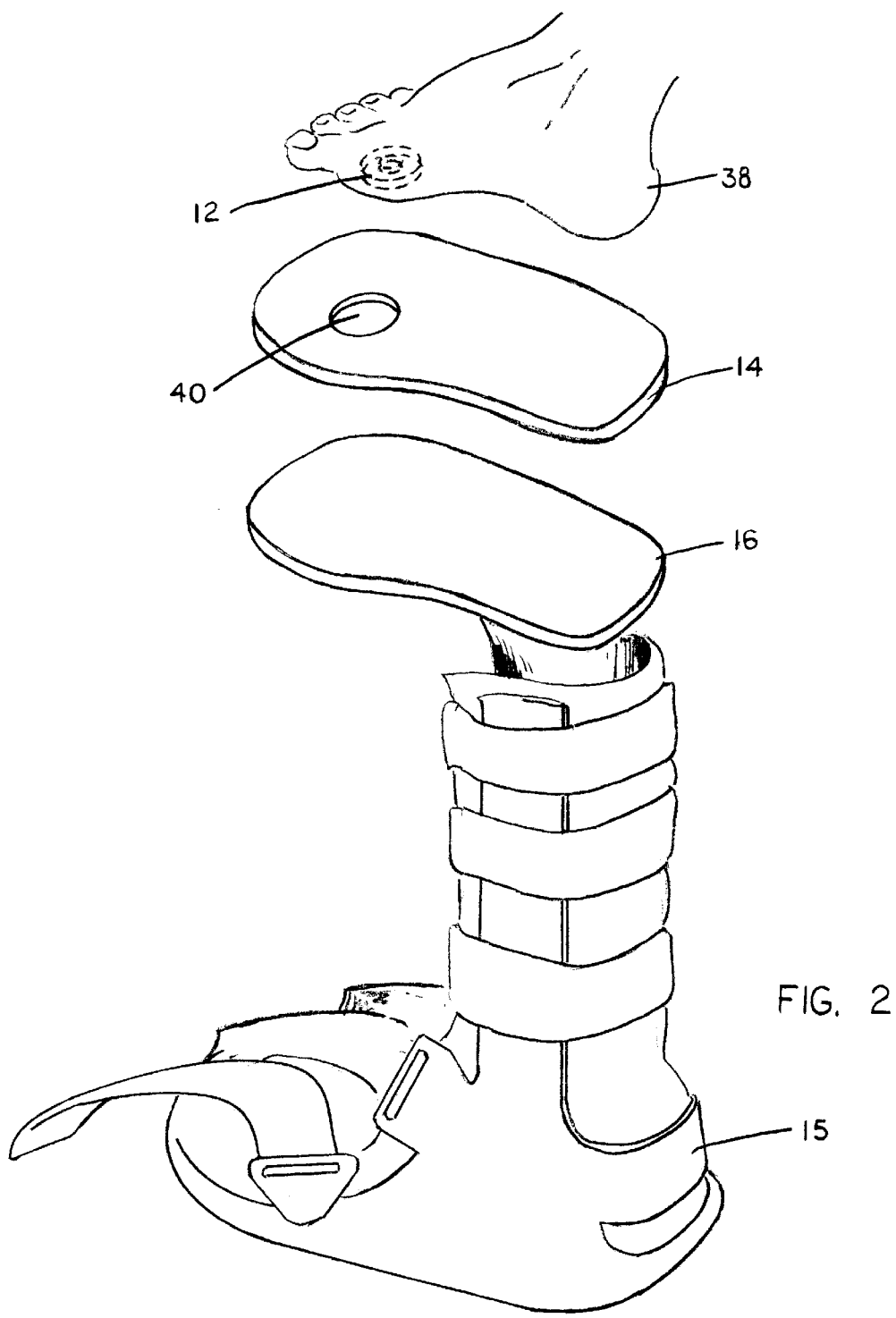
FIG. 2 is an exploded view of the wound healing system in use according to the present invention.
Figure 3:
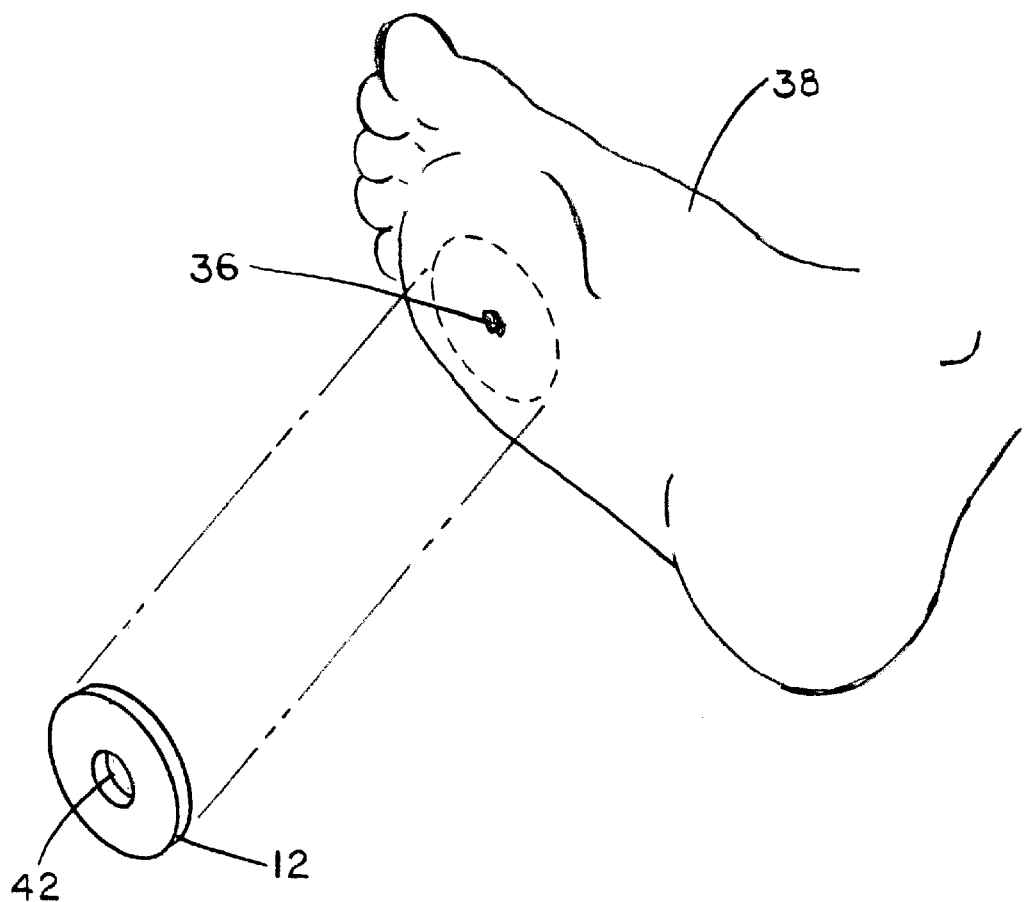
FIG. 3 is an exploded view of a load relieving dressing and a foot according to the present invention.
Figure 4:
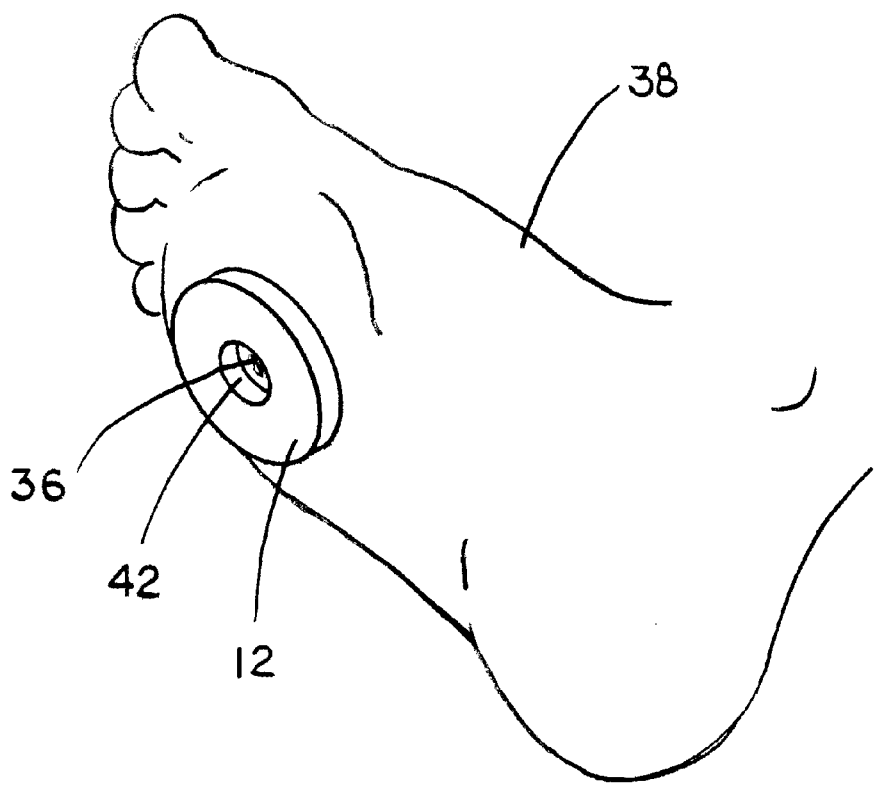
FIG. 4 is a perspective view of the load relieving dressing and a foot according to the present invention.

FIG. 2 shows the wound healing system 10 used on a typical foot wound 36, such as a plantar ulcer of a diabetic patient. Shown in FIGS. 2–4 is a load relieving dressing 12 applied to a bottom area of a foot 38 and about the wound 36. The load relieving dressing 12 supports the area of the foot 38 to which the load relieving dressing 12 is applied. The load relieving dressing 12 is usually applied to the foot 38 using some type of adhesive. The load relieving dressing 12 is inserted into a dressing opening 40 of the foot pad 14, when the foot 38 is placed on the foot pad 14. The dressing opening 40 is depicted in the figures as a hole, but can merely be an opening in the foot pad 14, which receives the load relieving dressing 12. The foot pad 14 is typically placed in a boot 15 as shown or in another type of shoe able to receive the foot pad 14. Additionally, a cushion pad 16 may be placed in the boot 15 before the foot pad 14 to provide additional protection and cushioning of the wound 36.

Figure 5:
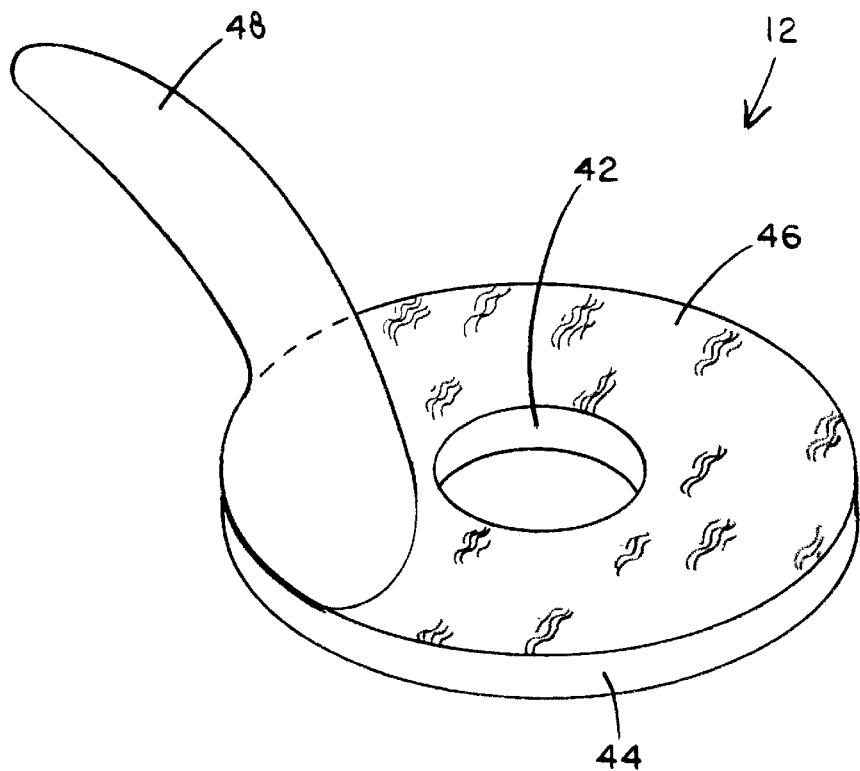
FIG. 5 is a perspective view of an example of the load relieving dressing according to the present invention.
Figure 6:
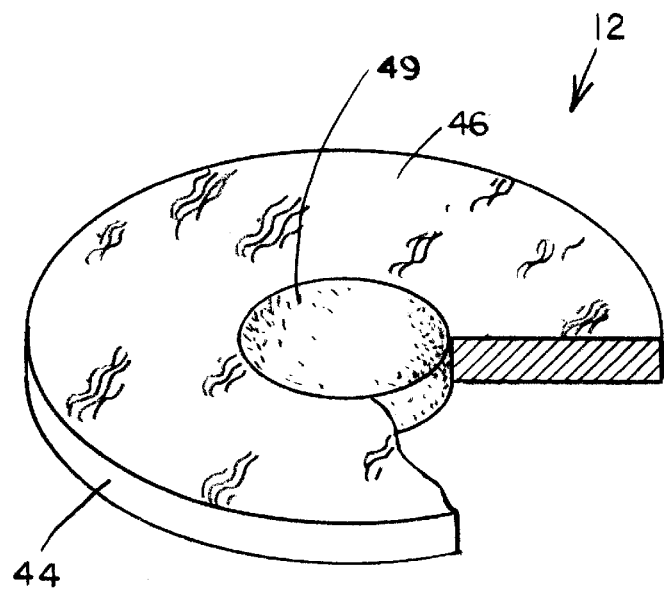
FIG. 6 is a perspective view of another example of the load relieving dressing according to the present invention.

FIGS. 5–27 show different types and sizes of padding, which can be used as the load relieving dressing 12. The load relieving dressing 12 can be made from any material or combination of materials that lend themselves to providing proper support to relieve load on the wound 36. These materials can soft or firm. An example of a material is felt foam padding. The load relieving dressing 12 includes a wound aperture 42 or a less dense material in place of the wound aperture 42 to relieve pressure or load on and around the wound 36. The wound aperture 42 or less dense material is usually in the center of the load relieving dressing 12. In all of the figures, the wound aperture 42 is shown as a hole, but could merely be an opening which relieves the load on the wound 36. The load relieving dressing 12 shown in FIG. 5 includes a round pad 44 with the wound aperture 42 cut out in the center of the round pad 44. The load relieving dressing 12 of FIG. 5 is also shown with an adhesive layer 46 and a removable protective layer 48, which protects the adhesive layer 46. FIG. 6 shows the round pad of FIG. 5 with the addition of an additional material 49 in the wound aperture 42. The additional material 49 has different physical properties to the pad employed, yet is beneficial to the wound 36. An example of an additional material 49 is a spongy material, which is a less dense material then the pad, allowing some support, yet still relieving the load on the wound 36.

Figure 9:
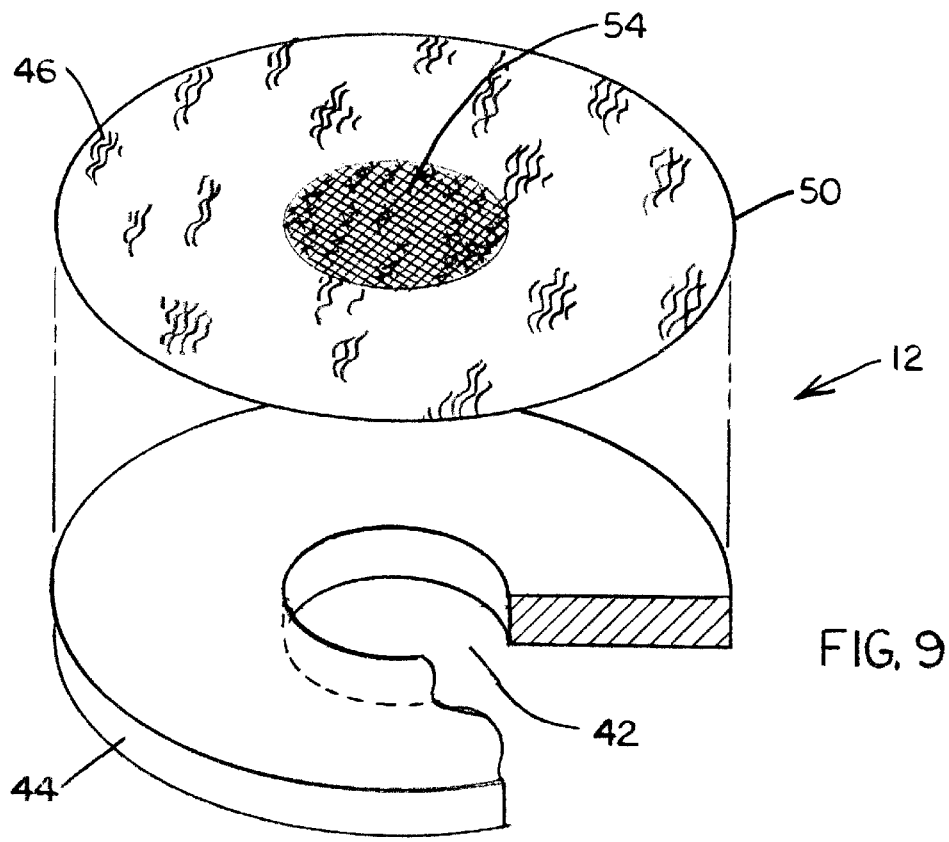
FIG. 9 is a perspective view of another example of the load relieving dressing according to the present invention.
Figure 10:
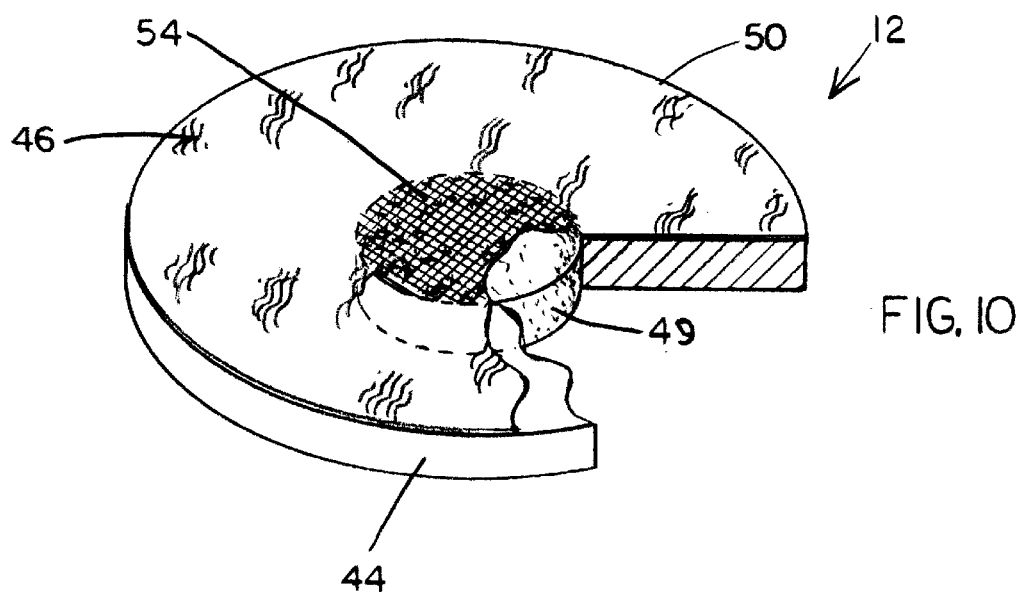
FIG. 10 is a perspective view of another example of the load relieving dressing according to the present invention.
Figure 11:
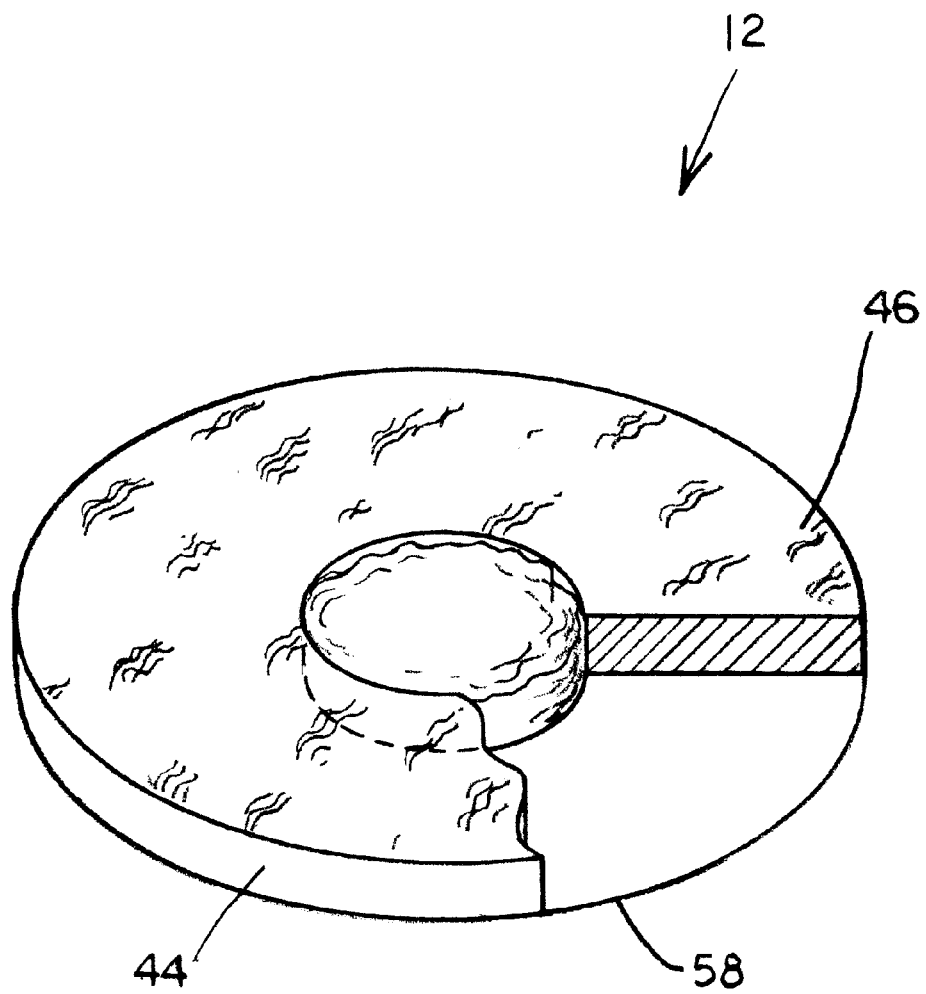
FIG. 11 is a perspective view of another example of the load relieving dressing according to the present invention.
Figure 12:
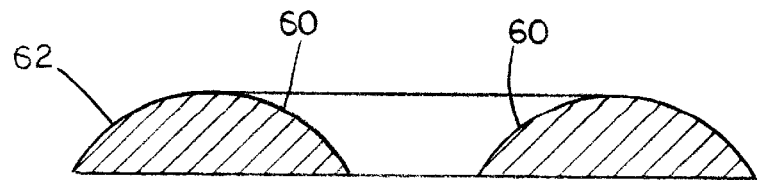
FIG. 12 is a cross-sectional view of an example of the load relieving dressing according to the present invention.
Figure 13:
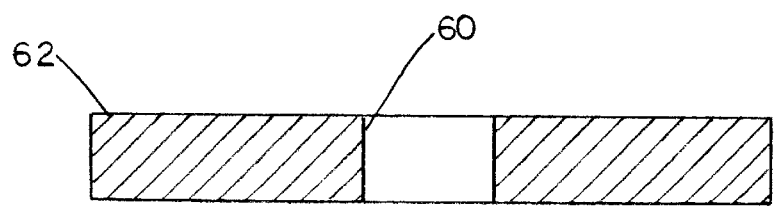
FIG. 13 is a cross-sectional view of another example of the load relieving dressing according to the present invention.
Figure 14:
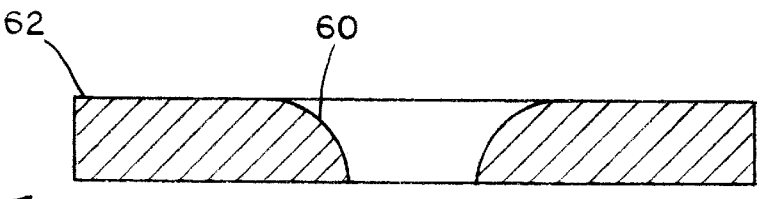
FIG. 14 is a cross-sectional view of another example of the load relieving dressing according to the present invention.
Figure 15:
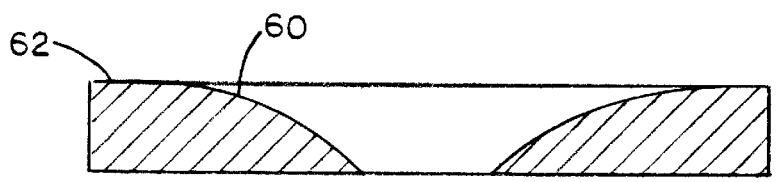
FIG. 15 is a cross-sectional view of another example of the load relieving dressing according to the present invention.

FIG. 7 shows the round pad 44 of FIG. 5, whereby the adhesive layer 46 is replaced with an adhesive sheet 50. The adhesive sheet 50 is attached to the top of the round pad 44. The adhesive sheet 50 includes a medicated center 52 which fits over the wound aperture 42 and acts as an occlusive dressing. The medicated center 52 can include medication to aid in the healing of the wound 36. FIG. 8 shows the round pad 44 of FIG. 7 with the additional material 49 in the wound aperture 42. FIG. 9 shows the round pad 44 of FIG. 7, whereby the adhesive sheet 50 includes a mesh center 54 over the wound aperture 42. The mesh center 54 is similar to bandage material to allow airflow and can be coated with medication. FIG. 10 shows the round pad 44 of FIG. 9 with the additional material 49 in the wound aperture 42. FIG. 11 shows the round pad 44 of FIG. 5 with the wound aperture 42 filled with medication 56 and a membrane 58 applied to the bottom of the pad 44. The membrane 58 is used to support the medication 56 in the wound aperture 42. FIGS. 12–15 show cross-sections of the round pad concept for the load relieving dressing 12, whereby the edge 60 of the wound aperture 42 in each case is different. FIG. 12 also shows a different outside edge 62 for the outside edging of the load relieving dressing 12. Different shaping of wound aperture edge 60 and the outside edge 62 of the load relieving dressing 12 can address different types of wounds and the variety of shapes provide for optimal pressure distribution at the periphery of the wound 36. All of the load relieving dressings 12 shown in concept in FIGS. 5–15 can be made as different shapes and sizes so that the correct dressing size and shape can be selected for wounds of different shapes and sizes.

Figure 16:
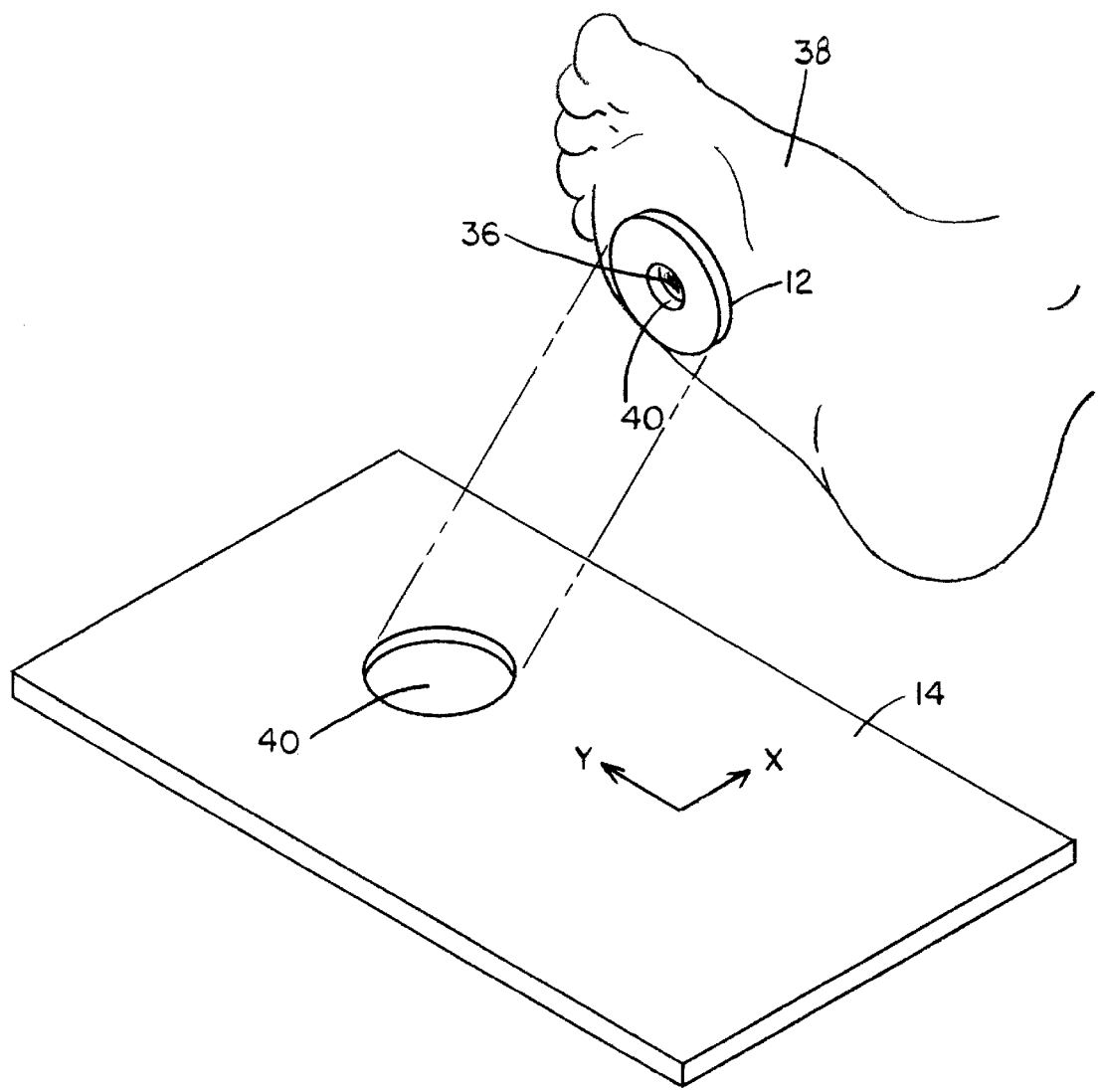
FIG. 16 is an exploded view of a load relieving dressing on a foot being placed in an uncut foot pad according to the present invention.
Figure 17:
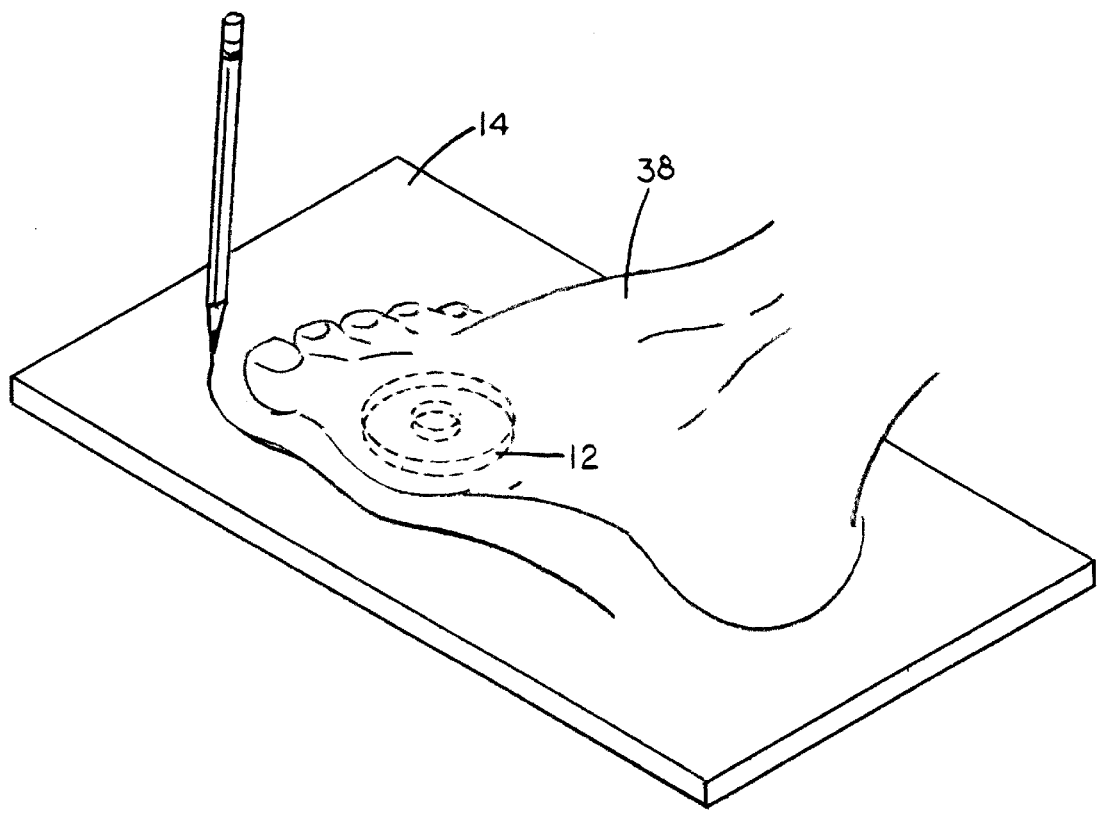
FIG. 17 is a perspective view of a load relieving dressing on a foot placed in the uncut foot pad according to the present invention.
Figure 18:
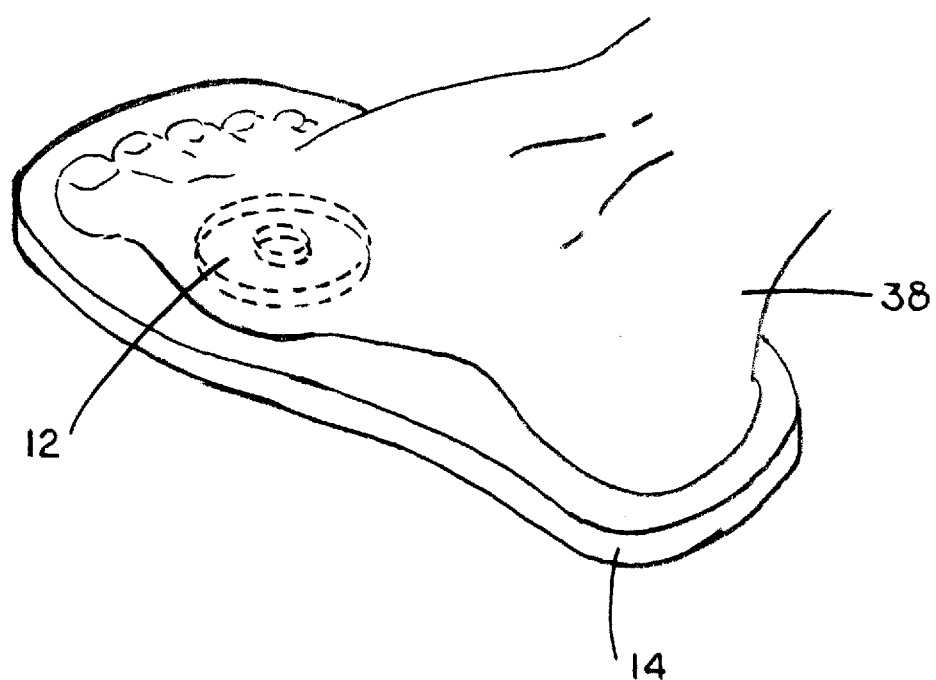
FIG. 18 is a perspective view of a load relieving dressing on a foot placed in a cut foot pad according to the present invention.
Figure 19:
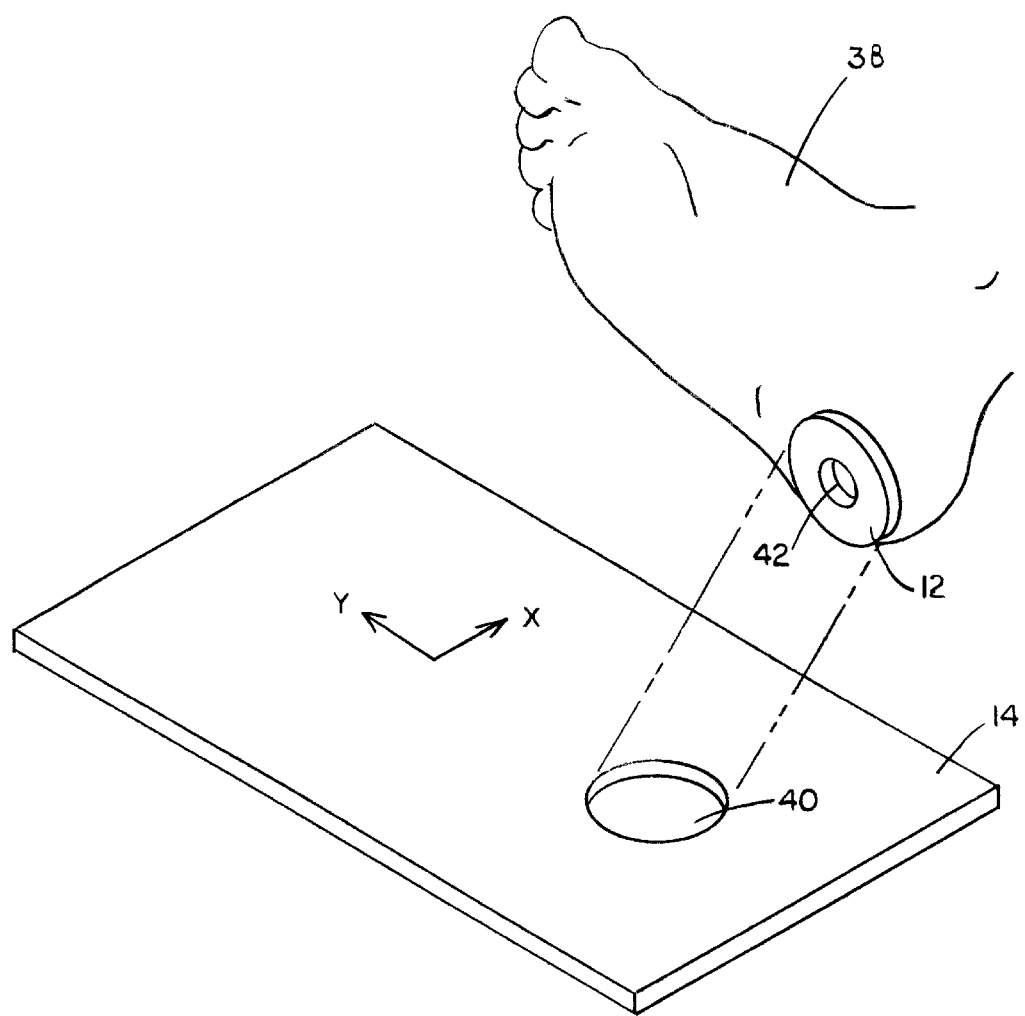
FIG. 19 is another exploded view of a load relieving dressing on a foot being placed in an uncut foot pad according to the present invention.
Figure 20:
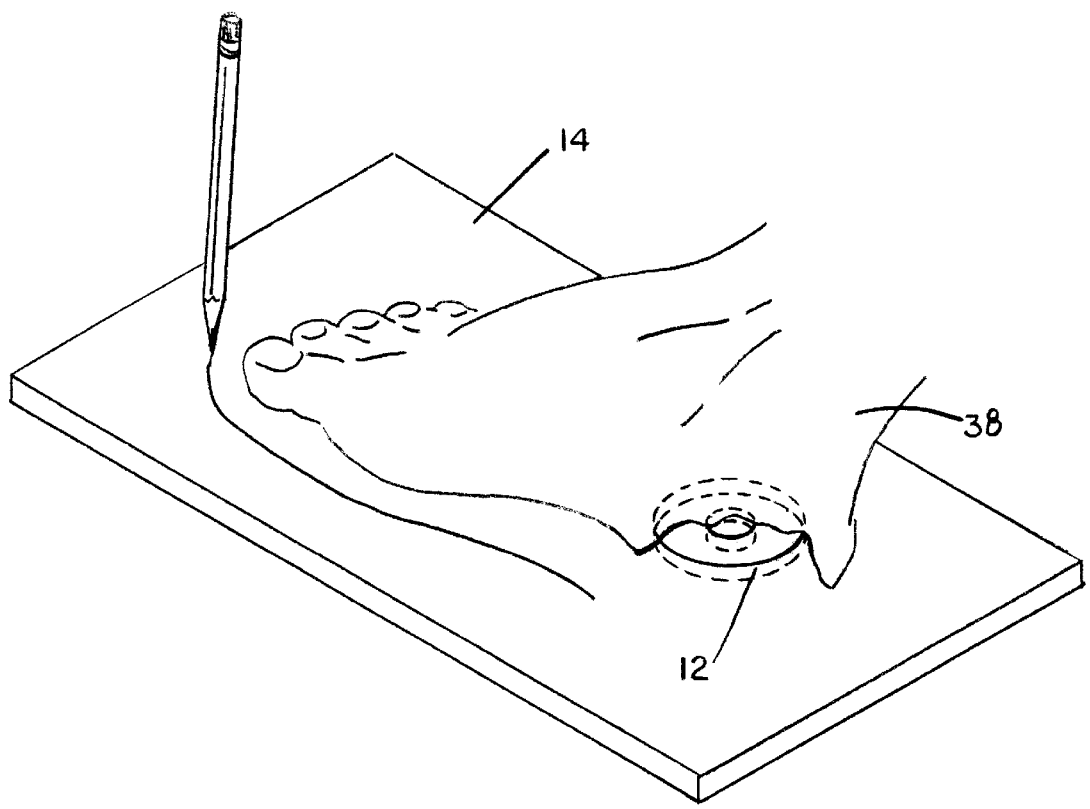
FIG. 20 is another perspective view of a load relieving dressing on a foot placed in the uncut foot pad according to the present invention.
Figure 21:
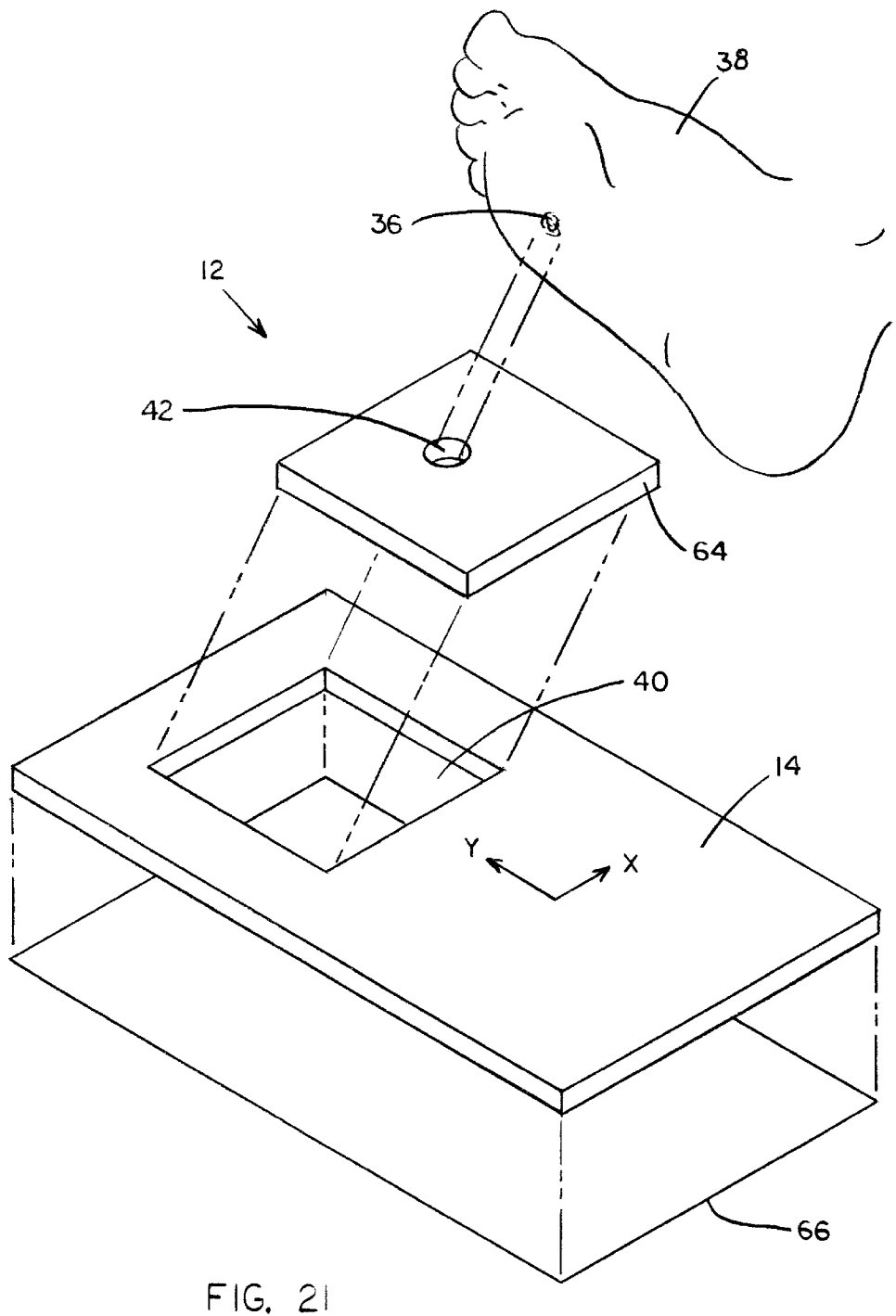
FIG. 21 is another exploded view of a load relieving dressing being placed on a foot, ready to be placed in an uncut foot pad according to the present invention.
Figure 22:
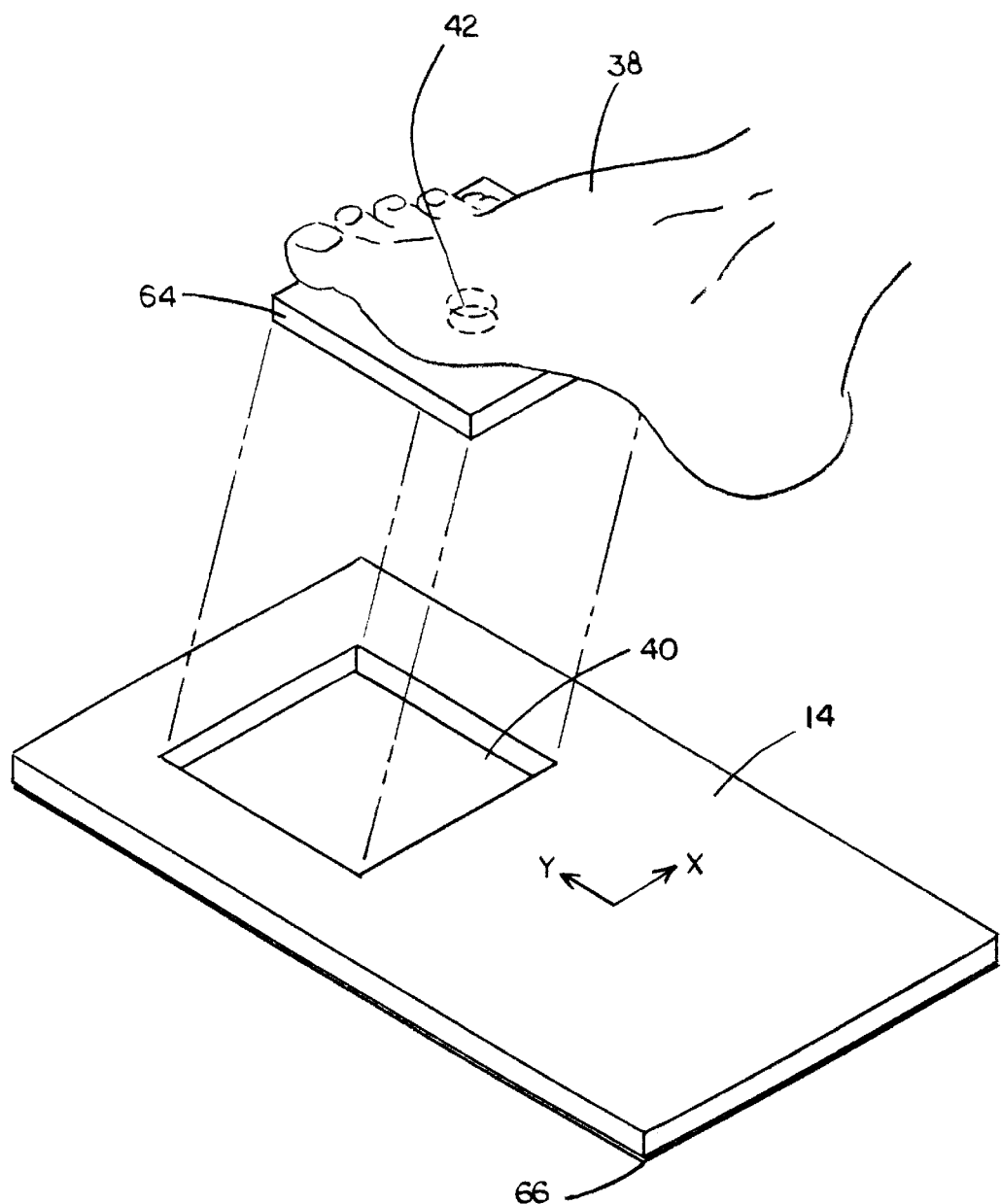
FIG. 22 is another exploded view of a load relieving dressing on a foot being placed in an uncut foot pad according to the present invention.
Figure 23:
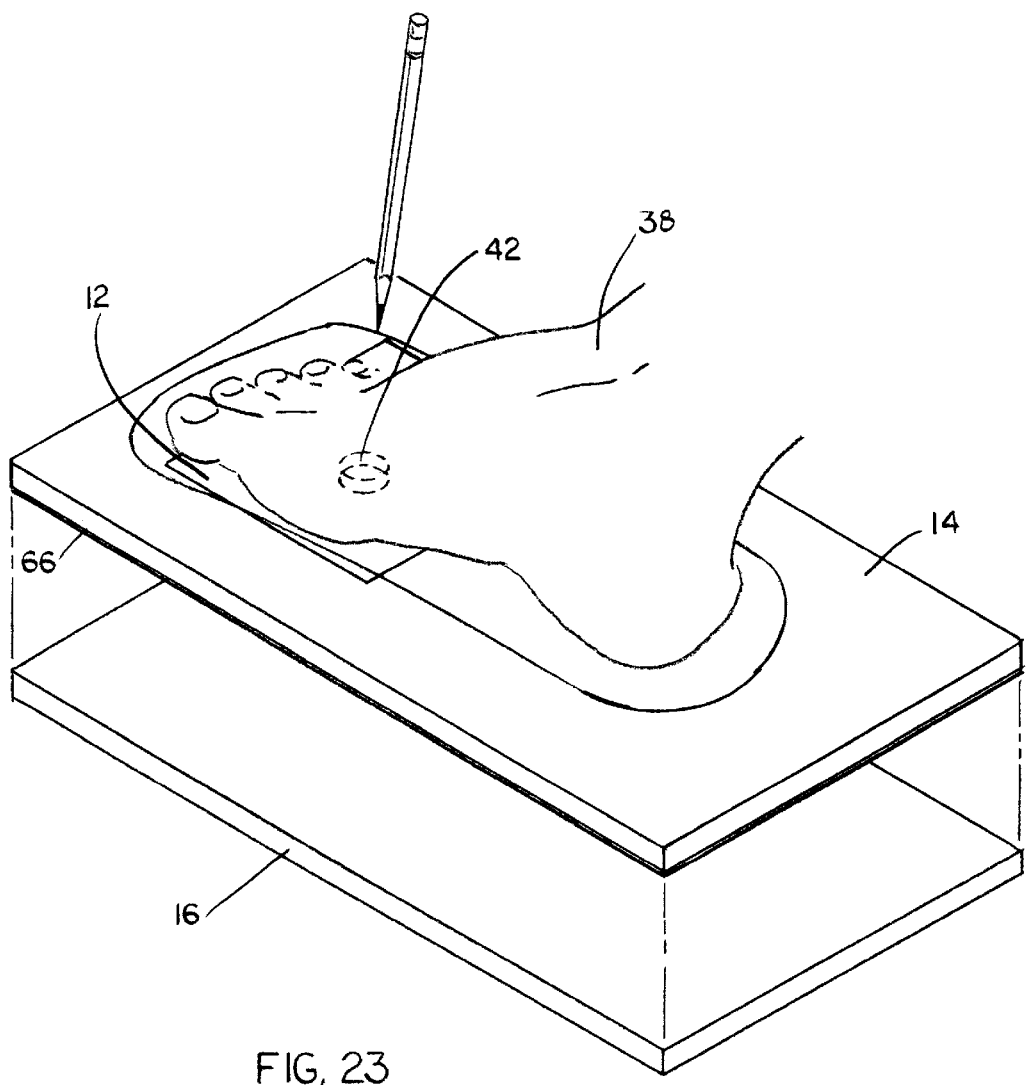
FIG. 23 is another perspective view of a load relieving dressing on a foot placed in an uncut foot pad according to the present invention.
Figure 24:
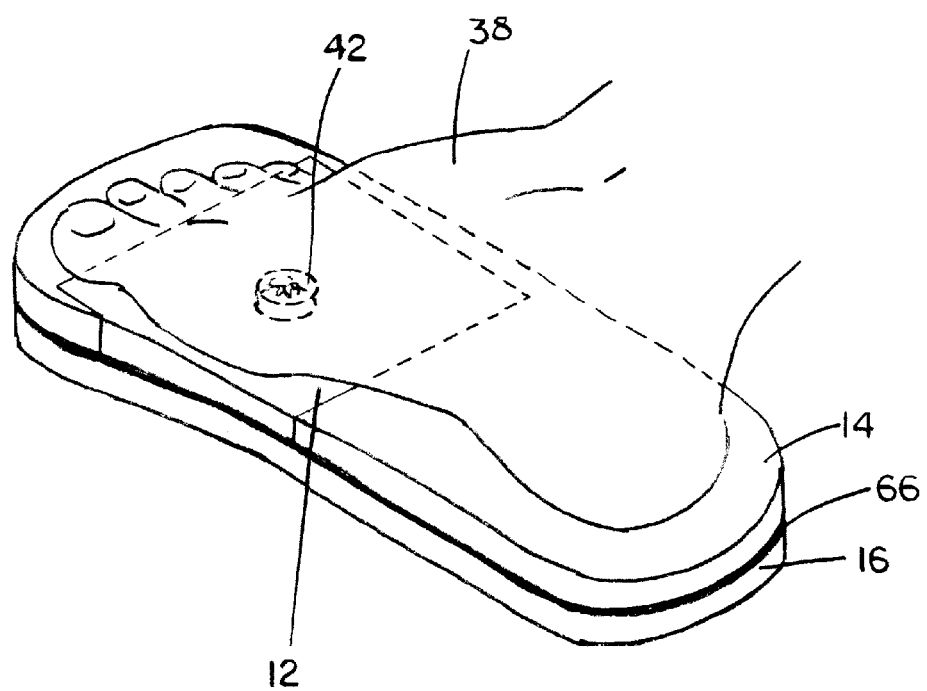
FIG. 24 is another perspective view of a load relieving dressing on a foot placed in a cut foot pad according to the present invention.

FIG. 16 shows the foot pad 14 uncut. The uncut foot pad 14 must be sized and cut according to the size of the foot 38 and the position of the wound 36 on the foot 38. The foot pad 14 can be made of any type of material or combinations of material which lend themselves to being inserted into footwear. The most likely material for the foot pad 14 would be a type of foam, which could be soft or firm. The foot pad 14 includes the dressing opening 40 which securely receives the load relieving dressing 12. The dressing opening 40 is usually offset from the center of the foot pad 14 in the y-direction, as shown in FIG. 16. The dressing opening 40 is positioned such that there is enough material to surround the foot 38, when the wound 36 is between the center of the foot 38 and either the toe or heel of the foot 38. Therefore, the foot pad 14 must be large enough in the x and y directions to accommodate a foot 38, regardless of the position of the wound 36. The foot 38 is placed on the uncut foot pad 14, such that the load relieving dressing 12 is inserted into the dressing opening 40, as shown in FIGS. 16–17. The outline of the foot 38 is then traced onto the foot pad 14, as shown in FIG. 17. The outline must be large enough to provide proper support of the foot 38 and proper fit in the boot 15. As in the case of the type of boot 15 shown in FIG. 2, the boot 15 is adjustable to accommodate many different sizes of feet. Finally, the foot pad 14 is cut along the outline of the foot 38 to produce a finished foot pad 14 as shown in FIG. 18. FIGS. 16–18 show placement of the foot 38 when the wound 36 is between the toes and the center of the foot 38. FIGS. 19–20 show a different positioning of the same uncut foot pad 14 in relation to the foot 38, if the wound 36 is between the heel and the center of the foot 38.

Figure 25:
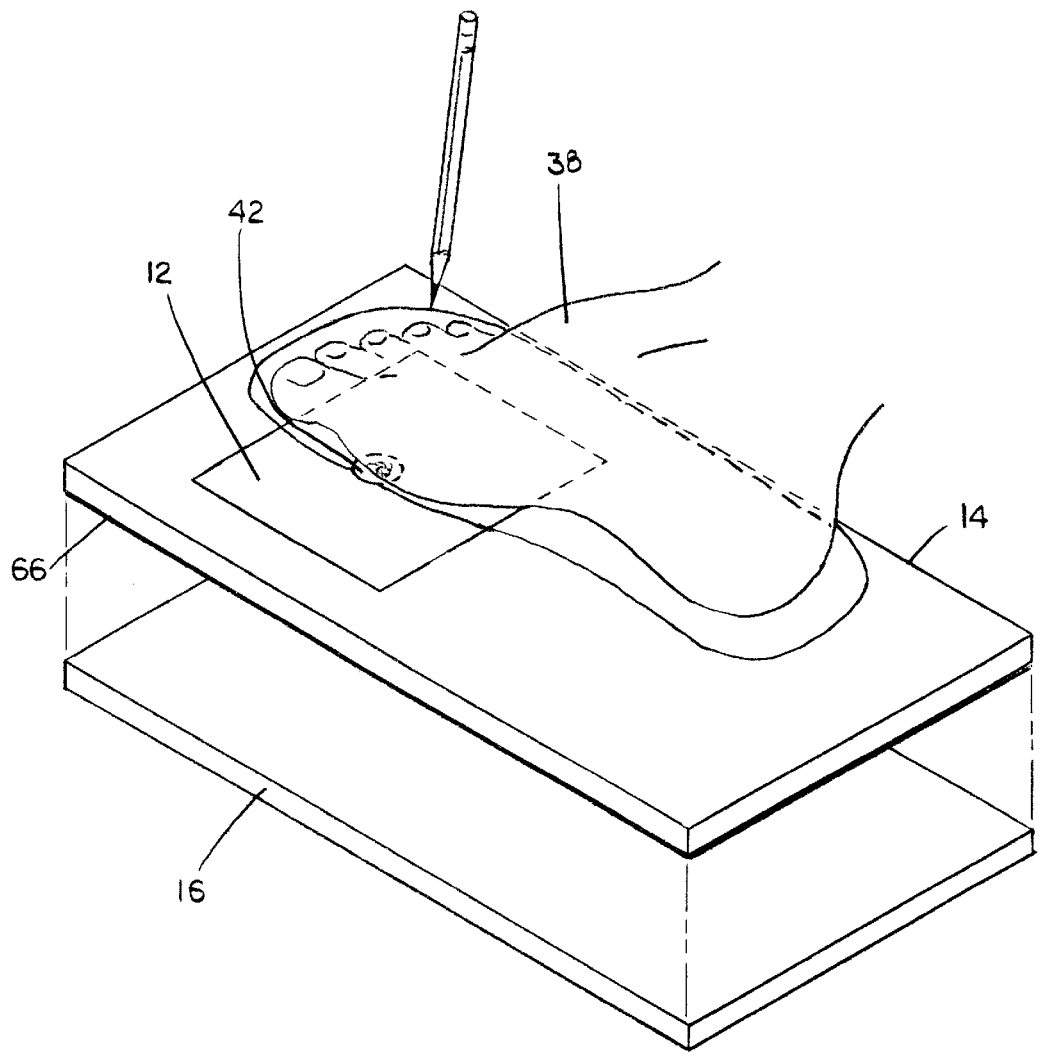
FIG. 25 is another perspective view of a load relieving dressing on a foot placed in an uncut foot pad according to the present invention.
Figure 26:
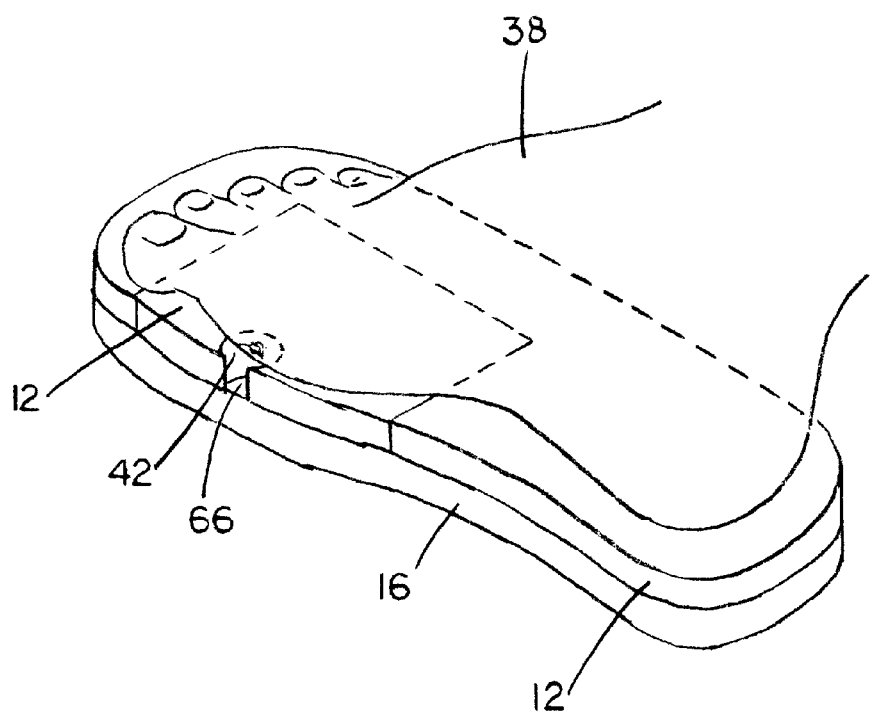
FIG. 26 is another perspective view of a load relieving dressing on a foot placed in a cut foot pad according to the present invention.
Figure 27:
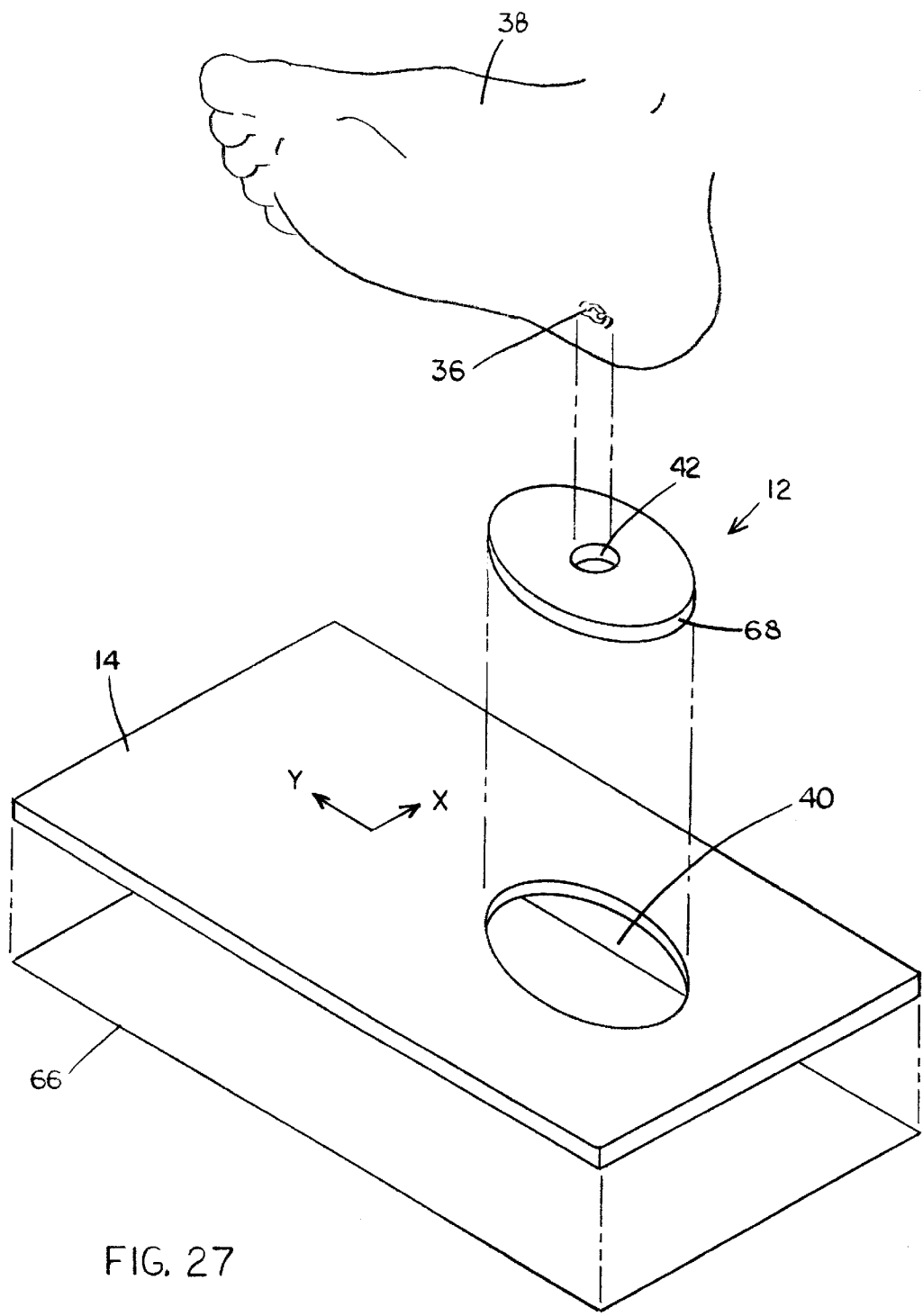
FIG. 27 is another exploded view of a load relieving dressing being placed on a foot, ready to be placed in an uncut foot pad according to the present invention.
Figure 28:
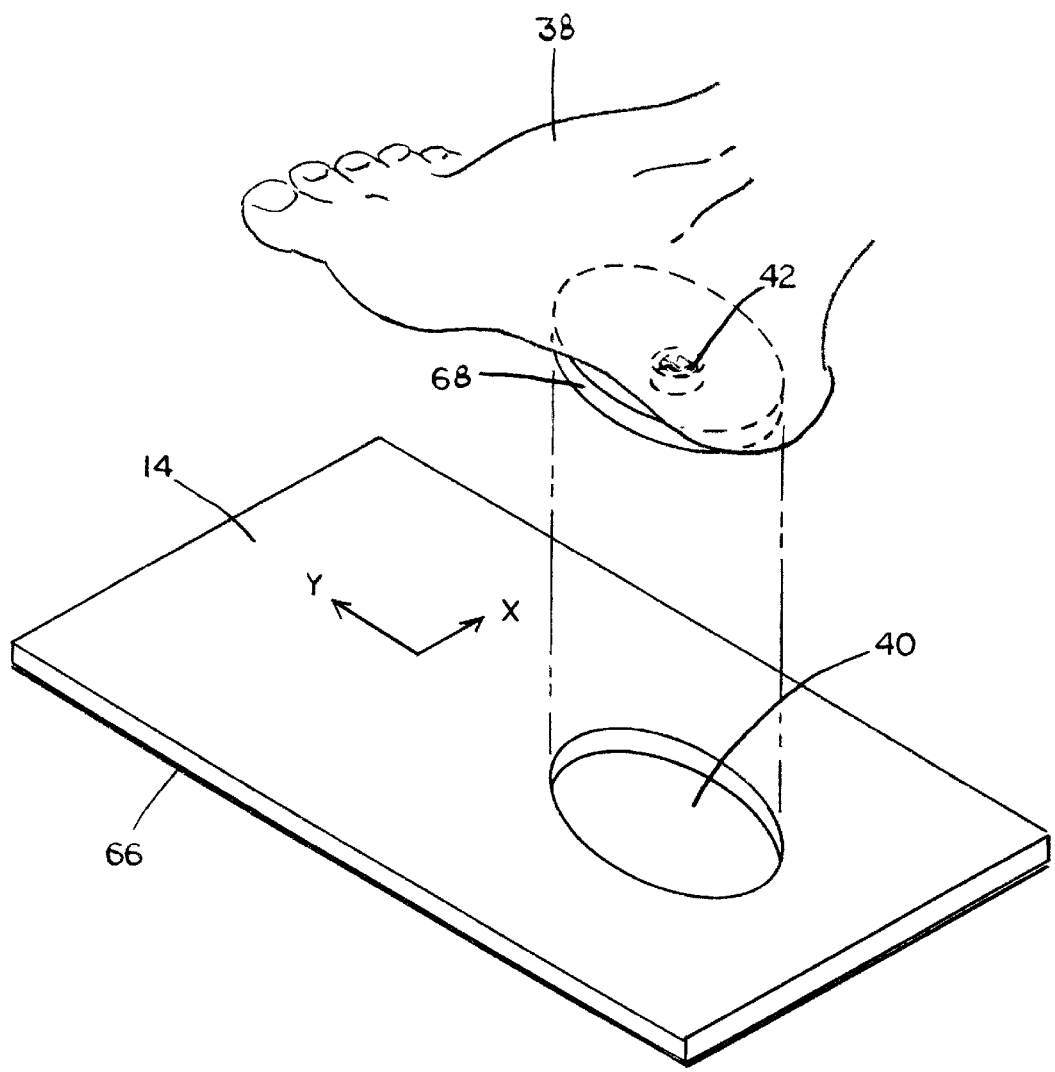
FIG. 28 is another exploded view of a load relieving dressing on a foot being placed in an uncut foot pad according to the present invention.
Figure 29:
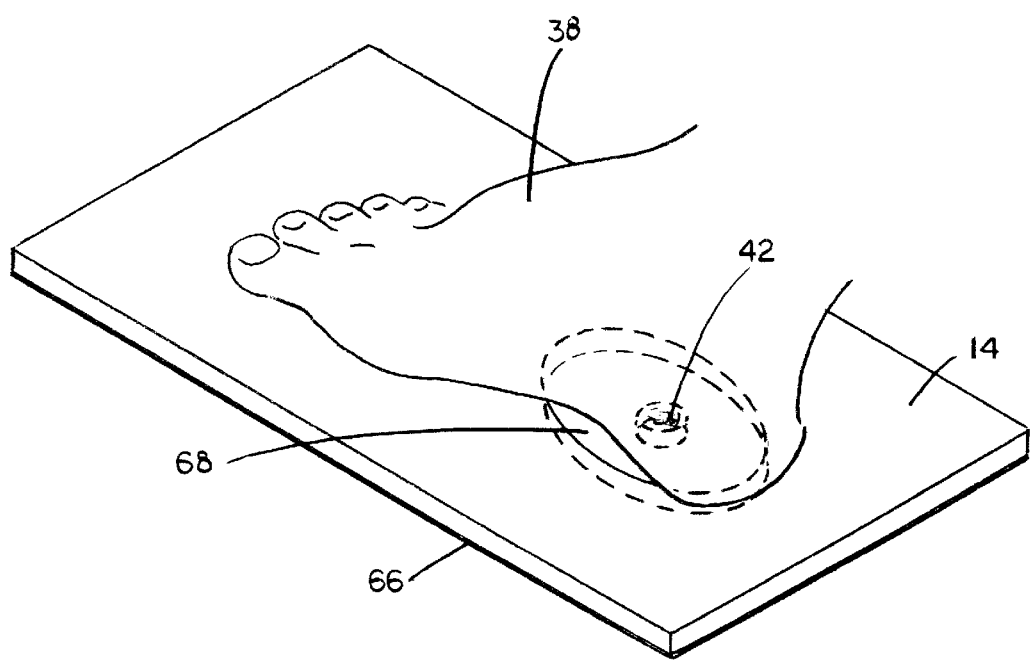
FIG. 29 is another perspective view of a load relieving dressing on a foot placed in a cut foot pad according to the present invention.

FIGS. 21–26 show the load relieving dressing 12 as a rectangular pad 64 with the round wound aperture 42. As shown in FIGS. 21–26, the rectangular pad 64 is attached to foot 38 and covers a greater area of the foot 38. The larger rectangular pad 64 provides a larger surface area for the patient to walk on, when the rectangular pad 64 is not inserted into the foot pad 14. This is important since it is anticipated that the patient will walk occasionally without the boot 15 and/or foot pad 14 and such walking in a barefoot state could retard the progress of healing. Having a large load relieving dressing 12 such as the rectangular pad 64 gives additional protection of the wound 36, when the boot 15 and foot pad 14 are not employed. The uncut foot pad 14 includes a rectangular dressing opening 40 to receive the rectangular pad 64. The uncut foot pad 14 is large enough in the x and y directions to accommodate a foot 38, regardless of the position of the wound 36. FIGS. 21–26 show the same process for cutting out the foot pad 14, as is shown in FIGS. 16–18. FIGS. 25–27 show the positioning of the foot 38 and the cut foot pad 14, if the wound 36 is close to the side of the foot 38. Also, shown in FIGS. 21–26 are a foot pad support sheet 66 and an uncut cushion pad 16. The foot pad support sheet 66 is a sheet of flexible, yet rigid material attached to the bottom of the uncut foot pad 14. Integrity of the foot pad 14 needs to be maintained, even if the edge of the dressing opening 40 must be cut away from the foot pad 14 to position the foot 38 correctly in the boot 15. The foot pad support sheet 66 provides support to maintain the integrity of the foot pad 14 in such cases. The uncut cushion pad 16 is placed under the foot pad 14 before cutting, so the cushion pad 16 may be cut out to the same size as the foot pad 14, if a pre-cut cushion pad 16 to fit the boot 15 is not provided. FIGS. 21–26 show the placement of the foot 38, if the wound 36 is between the toes and the center of the foot 38. FIGS. 27–29 show an oval shaped pad 68 used as the load relieving dressing 12 and an oval shaped dressing opening 40 in the foot pad 14. FIGS. 27–29 also show the placement of the foot 38, if the wound 36 is between the heel and the center of the foot 38.

Some of the key features of the present invention are that it provides a wound healing system which allows the patient more freedom and mobility. More freedom and mobility translates to accepted use by the patient before the wound progresses into a wound which can not be healed. The wound aperture 42 or the less dense material in the center of the load relieving dressing 12 provides the reduction of load on the wound 36, thereby aiding in the healing of the wound 36. The ability to engage and disengage the load relieving dressing 12 from the foot pad 14 allows the patient to remove the more bulky parts of the system, if necessary. Examples of when the foot pad 14 and boot 15 may be removed are when the patient is resting or bathing. Under these circumstances of limited weight-bearing, the load relieving dressing 12 itself will off-load the wound enough to permit healing, even if some steps are taken without the boot 15 and foot pad 14. The geometric shapes of the wound aperture 42, load relieving dressing 12 and the dressing opening 40 can be changed to suit different situations and wounds.

The kit, as described above, provides an easy system for medical staff to employ in the treatment of a wound. The medical staff can simply open the box and find all the elements necessary for wound treatment and healing and follow an instruction manual to treat the wound. The instruction manual can be part of the educational materials. Basically, the kit allows the medical staff to clean the wound using the wound cleanser 28, wound treatment pads 26, surgical blade 18 and tweezers 20. The ruler 24 or other measuring instrument is used to assess the size of the wound and track the healing progress of the wound. The load relieving dressing 12 is prepared by the staff, depending of the type of load relieving dressing 12. The most appropriate load relieving dressing 12 is selected based on wound type and wound size, which include the choices of various medicated centers. The most appropriate size and shape of the load relieving dressing 12 is selected and may be cut to size, and preparation may include removing protective coverings and applying medication. Then, the load relieving dressing 12 can be applied to foot 38. After the load relieving dressing 12 is applied, the foot 38 is placed on the foot pad 14 to outline the foot 38. The foot pad 14 is cut according to the outline, whereby the ruler 24 and the scissors 22 are employed. If the cushion pad 16 is to be employed, it must be cut, unless it comes in the kit as a pre-cut item. The cushion pad 16 and foot pad 14 are then placed into the boot 15, whereby the wound healing system 10 is ready for use by the patient. It is expected that the load relieving dressing 12 will be changed on a regular basis, so that the wound may be treated and examined.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of any and all equivalents thereof.

We claim:

1. A wound healing system for healing a wound on a foot of a patient comprising:
   a load relieving dressing adapted to be attached to an area about the wound of the foot, whereby said load relieving dressing is adapted to provide support to the foot in the area and relieves load on the wound;
   an adhesive applied to said toad relieving dressing which is adapted to attach said load relieving dressing to the foot; and a foot pad for footwear, said foot pad being a planer flat surface adapted to be under the foot; and a dressing opening in said foot pad, said dressing opening sized to securely receive said load relieving dressing, said dressing opening and said load relieving dressing configured to allow easy removal of said load relieving dressing attached to the foot by pulling the foot away from said foot pad.

2. The wound healing system of claim 1, further including a wound aperture as part of said load relieving dressing to relieve a load placed on the wound when the patient walks.

3. The wound healing system of claim 2, wherein said wound aperture is an open through hole through a top and bottom of said load relieving dressing.

4. The wound healing system of claim 1, further including footwear to receive said foot pad.

5. The wound healing system of claim 1, further including a cushion pad to provide support for said foot pad in footwear.

6. The wound healing system of claim 1, wherein said load relieving dressing is large enough to provide support along a width of the foot in said area.

7. The wound healing system of claim 1, wherein said foot pad is large enough to accommodate the foot due to placement of the wound in relation to said load relieving dressing and said dressing opening, such that said foot pad can be cut to shape of the foot in order to allow said foot pad to fit in footwear.

8. The wound healing system of claim 1, wherein said load relieving dressing includes medication which contacts the wound.

9. The wound healing system of claim 1, wherein said load relieving dressing includes a bandage type material which contacts the wound.

10. The wound healing system of claim 1, wherein said load relieving dressing includes a material other than air that contacts the wound which is less dense than material of said load relieving dressing which surrounds the wound.

11. The wound healing system of claim 1, wherein said load relieving dressing and said dressing opening are round.

12. The wound healing system of claim 1, wherein said load relieving dressing and said dressing opening are rectangular.

13. The wound healing system of claim 1, wherein said load relieving dressing and said dressing opening are oval.

14. The wound healing system of claim 1, wherein said foot pad includes a foot pad support sheet attached to said foot pad about said dressing opening, said foot pad support sheet at least larger than said dressing opening in order to provide support and maintain integrity of said foot pad if said foot pad has a portion cut away in an area of said dressing opening.

15. A kit for healing a wound on a foot, comprising:

a load relieving dressing adapted to be attached to an area about the wound of the foot, whereby said load relieving dressing is adapted to provide support to the foot in the area and relieves load on the wound;

an adhesive applied to said load relieving dressing which is adapted to attach said load relieving dressing to the foot; and a foot pad for footwear, said foot pad being a planer flat surface adapted to be under the foot; and a dressing opening in said foot pad, said dressing opening sized to securely receive said load relieving dressing, said dressing opening and said load relieving dressing configured to allow easy removal of said load relieving dressing attached to the foot by pulling the foot away from said foot pad.

16. The kit of claim 15, further including at least one measuring instrument to allow measurement of the wound and foot.

17. The kit of claim 15, further including at least one cutting instrument to cut said foot pad.

18. The kit of claim 15, further including at least one attending instrument to attend to the wound on the foot.

19. The kit of claim 15, further including educational materials to educate on application and use of said kit.

* * * * *